(12) United States Patent
Minoda et al.

(10) Patent No.: US 9,234,881 B2
(45) Date of Patent: Jan. 12, 2016

(54) SAMPLE DETECTION METHOD BY THIN-LAYER CHROMATOGRAPHY, THIN-LAYER CHROMATOGRAPHY PLATE, AND METHOD FOR PRODUCING SAME

(75) Inventors: Toshiharu Minoda, Myoko (JP); Isamu Ikeda, Myoko (JP); Satoru Nose, Myoko (JP); Noriaki Takeya, Myoko (JP); Ichiro Okamoto, Osaka (JP)

(73) Assignee: DAICEL CORPORATION, Osaka-shi, Osaka (JP)

(*) Notice: Subject to any disclaimer, the term of this patent is extended or adjusted under 35 U.S.C. 154(b) by 320 days.

(21) Appl. No.: 13/700,223

(22) PCT Filed: May 27, 2011

(86) PCT No.: PCT/JP2011/062173
§ 371 (c)(1),
(2), (4) Date: Nov. 27, 2012

(87) PCT Pub. No.: WO2011/149041
PCT Pub. Date: Dec. 1, 2011

(65) Prior Publication Data
US 2013/0067996 A1    Mar. 21, 2013

(30) Foreign Application Priority Data
May 27, 2010 (JP) .................. 2010-121140

(51) Int. Cl.
*G01N 30/90* (2006.01)
*G01N 30/94* (2006.01)
*G01N 30/92* (2006.01)

(52) U.S. Cl.
CPC ............. *G01N 30/90* (2013.01); *G01N 30/92* (2013.01); *G01N 30/94* (2013.01); *G01N 2030/945* (2013.01)

(58) Field of Classification Search
CPC ........ G01N 30/94; G01N 30/90; G01N 30/91
USPC ........................................ 73/61.54
See application file for complete search history.

(56) References Cited

U.S. PATENT DOCUMENTS 4,313,906 A    2/1982  Filipi et al.
6,331,254 B1 *  12/2001  White et al. .................. 210/658
(Continued)

FOREIGN PATENT DOCUMENTS

JP    56-037057    4/1981
JP    05-232099    9/1993
(Continued)

OTHER PUBLICATIONS

International Search Report of PCT/JP2011/062173 (2 pages).
(Continued)

*Primary Examiner* — Hezron E Williams
*Assistant Examiner* — Rodney T Frank
(74) *Attorney, Agent, or Firm* — Flynn, Thiel, Boutell & Tanis, P.C.

(57) ABSTRACT

A thin-layer chromatography plate and a thin-layer chromatography uses a thin-layer chromatography plate that has a first separating agent layer, which has the same optical response as the sample, and a second separating agent layer, which is disposed adjacent thereto and has an optical response that is different from the aforementioned optical response; carries out development of the sample in the first separating agent layer; thereafter carries out further development of the spots from the first separating agent layer toward the second separating agent layer; and detects the spots in the second separating agent layer through exposure to ultraviolet radiation or a color-development treatment with a coloring agent.

3 Claims, 5 Drawing Sheets

(56) References Cited

U.S. PATENT DOCUMENTS

| | | |
|---|---|---|
| 6,485,687 B1 * | 11/2002 | Spangenberg et al. .... 422/82.05 |
| 6,528,322 B1 | 3/2003 | Carlsson et al. |
| 6,902,889 B1 | 6/2005 | Carlsson et al. |

FOREIGN PATENT DOCUMENTS

| | | |
|---|---|---|
| JP | 3140138 | 12/2000 |
| JP | 2009-25315 A | 2/2009 |
| WO | WO 01/11355 A1 | 2/2001 |
| WO | WO 03/022392 A1 | 3/2003 |

OTHER PUBLICATIONS

Search Report in European Patent Office issued in Application No. EP 11 78 6738 dated Jun. 17, 2014 (5 pages).

Japanese Office Action dated Sep. 29, 2015, including English translation thereof (10 pages).

* cited by examiner

SAMPLE DETECTION METHOD BY THIN-LAYER CHROMATOGRAPHY, THIN-LAYER CHROMATOGRAPHY PLATE, AND METHOD FOR PRODUCING SAME

BACKGROUND OF THE INVENTION

Field of the Invention

The present invention relates to a thin-layer chromatography plate (also referred to below as a "TLC plate") that has two types of separating agent layers that differ in their optical response to ultraviolet light or a coloring agent, to a method of producing this thin-layer chromatography plate, and to a method of using this thin-layer chromatography plate.

Thin-layer chromatography (also referred to below as "TLC") is known as a method for separating and detecting a particular component from a mixture. The separation of a component by TLC is detected, for example, based on a difference in optical response between the separating agent layer and the detection target component, by subjecting a spot provided by the development of a sample to exposure to ultraviolet light or to a color-development treatment with a coloring agent.

On the other hand, separating agents that contain a polysaccharide derivative, for example, the phenyl ester of a polysaccharide, are known as separating agents for optical isomers. Detection of the detection target component by exposure to ultraviolet light or a color-development treatment with a coloring agent may not be possible when such an aromatic ring-containing separating agent is used in the separating agent layer of the TLC plate.

Such a TLC plate is known in the form of a TLC plate in which a filler layer for optical resolution is disposed on a portion of the surface of a support on a flat plate (refer, for example, to Japanese Patent Publication No. 3140138). With this TLC plate, a filler layer for optical resolution and a silica gel-based filler layer are formed on the surface of a single support; a component (spot) separated on the filler layer for optical resolution is additionally developed into the silica gel-based filler layer; and the detection target component is detected by subjecting the silica gel-based filler layer to exposure to ultraviolet light or a color-development treatment with a coloring agent.

With this TLC plate, an extract component, which is readily adsorbed by the filler layer for optical resolution, migrates from the filler layer for optical resolution to the silica gel-based filler layer less satisfactorily than does a raffinate component, which is resistant to adsorption by the filler layer for optical resolution, and a satisfactory detection of the extract component in the silica gel-based filler layer may then not be possible and a determination of the state of separation by the filler layer for optical resolution may thus also not be possible. Due to this, this TLC plate may not be able to provide the necessary information when applied to an examination of the conditions for optical resolution by other types of chromatography, e.g., column chromatography, and there is thus still room for investigation on this point.

SUMMARY OF THE INVENTION

The present invention provides a TLC plate and TLC that can detect the separation of a component in a sample that has been brought about by a separating agent layer that does not permit the detection of the separation of the component in the sample by an optical response.

The present inventors carried out intensive investigations of the use in TLC composed of separating agents that have an optical response to ultraviolet light or a coloring agent and discovered a method wherein—by subjecting the spots provided by development in a first separating agent layer that has a particular such optical response to development in a direction different from this development direction and carrying out further development into a second separating agent layer that is adjacent to the first separating agent layer and that does not have the aforementioned optical response—the positional relationship of the spots in the development direction in the first separating agent layer is maintained in the second separating agent layer. The present invention was achieved based on this discovery.

Thus, the present invention provides a method that uses a TLC plate having a first separating agent layer and a second separating agent layer adjacent thereto and that detects a component in a sample that exhibits an optical response to ultraviolet light or a coloring agent, the method comprising a step of developing the sample in the first separating agent layer in a direction along the boundary between the first and second separating agent layers; a step of drying a mobile phase in at least the second separating agent layer; a step of changing the orientation of the TLC plate and developing a spot in the first separating agent layer into the second separating agent layer; and a step of detecting a spot that has migrated into the second separating agent layer by exposure to ultraviolet light or by a color-development treatment with a coloring agent, wherein the first separating agent layer is formed by a first separating agent, which has the optical response; the second separating agent layer is formed by a second separating agent, which has an optical response that is different from that of the first separating agent; and the optical response of the component is the same as the optical response of the first separating agent.

The present invention also provides a TLC plate that has a first separating agent layer, whose direction of development is a first direction, and, in a second direction that is orthogonal to the first direction, a second separating agent layer adjacent to the first separating agent layer, wherein the first separating agent layer is formed by a first separating agent, which has an optical response to ultraviolet light or a coloring agent;

the second separating agent layer is formed by a second separating agent, which has an optical response that is different from that of the first separating agent; and when a spot has been developed in a first direction in the first separating agent layer, a ratio of the spot migration distance $W2$ in a second direction in the first separating agent layer to the spot migration distance $W1$ in the first direction in the first separating agent layer is not more than $\pm 0.5$.

The present invention additionally provides the above-described method and the above-described TLC plate, wherein in each case the first separating agent is a separating agent for optical isomers.

The present invention further provides the above-described method and the above-described TLC plate, wherein in each case the separating agent for optical isomers is comprised of a polysaccharide derivative comprising a polysaccharide and an aromatic ester group, aromatic carbamoyl group, aromatic ether group, or carbonyl group substituted for all or a portion of the hydroxyl groups or amino groups in the polysaccharide.

The present invention additionally provides a method of producing a TLC plate that has a first separating agent layer and adjacent thereto a second separating agent layer, the method comprising a step of forming the first separating agent layer by coating a support with a first slurry that contains a coating solvent and a first separating agent, the first separating agent having an optical response to ultraviolet light or a coloring agent; and a step of forming the second separating agent layer adjacent to the first separating agent layer, by coating the support with a second slurry that contains a coating solvent and a second separating agent, the second separating agent having an optical response as described above that is different from that of the first separating agent, wherein the same type of coating solvent is used for the first and second slurries.

Because spots that have been developed in the first direction in the first separating agent layer migrate into the second separating agent layer while maintaining the positional relationship of the spots in the first direction, the present invention enables the detection of the separation of a component in the sample by a separating agent layer that does not permit the detection of the separation of the component in the sample by an optical response.

Moreover, because in the present invention the permissible migration width by the spots relative to the development direction is specified in a prescribed range for the first separating agent layer of the TLC plate, the present invention makes it possible to accurately comprehend, in the second separating agent layer, the state of separation of a component in the development direction in the first separating agent layer.

In addition, because the present invention provides for uniformity in the type of coating solvent for the first and second slurries, the present invention can provide a TLC plate that exhibits an excellent behavior for spot migration from the first separating agent layer to the second separating agent layer.

Further features of the present invention will become apparent from the following description of exemplary embodiments (with reference to the attached drawings).

DESCRIPTION OF THE EMBODIMENTS

The sample detection method of the present invention is a method that uses a TLC plate having a first separating agent layer and adjacent thereto a second separating agent layer and that detects a component in a sample that exhibits an optical response to ultraviolet light or a coloring agent. The detection method of the present invention comprises a step of developing the sample in the first separating agent layer in a direction along the boundary between the first and second separating agent layers; a step of drying the mobile phase in at least the second separating agent layer; a step of changing the orientation of the TLC plate and developing a spot in the first separating agent layer into the second separating agent layer; and a step of detecting a spot that has migrated into the second separating agent layer by exposure to ultraviolet light or by a color-development treatment with a coloring agent.

The step of developing the sample in the first separating agent layer in a direction along the boundary between the first and second separating agent layers (the first step) can be carried out in the same manner as in ordinary TLC with the exception that the sample is developed only within the first separating agent layer along the second separating agent layer. That is, this first step can be carried out by applying a spot of the sample to the first separating agent layer; as necessary drying the sample spot; using the direction that runs along the boundary between the first and second separating agent layers (also referred to as the "first direction") for the vertical direction; placing the edge of the sample-spotted separating agent at the bottom and immersing the edges of the first and second separating agent layers in the mobile phase; and developing the sample in the first separating agent layer.

The step of drying the mobile phase in at least the second separating agent layer (the second step) can be carried out in the same manner as drying of the mobile phase in ordinary TLC. Once the second separating agent layer has been dried in this second step, spot migration to the second separating agent layer can then be performed; however, drying of the mobile phase is preferably carried out on both the second separating agent layer and the first separating agent layer from the standpoint of stopping the enlargement and preserving the positional relationship of the spots in the first separating agent layer. When the mobile phase contains a flammable organic solvent, the second step is preferably carried out by air drying in proximity to a local exhaust arrangement from the standpoint of preventing combustion and toxicity. The second step may be carried out under reduced pressure.

The step of changing the orientation of the TLC plate and developing the spots in the first separating agent layer into the second separating agent layer (the third step) can be performed in the same manner as for ordinary TLC, with the exception that the spots in the first separating agent layer are developed into the second separating agent layer. That is, this third step can be performed by changing the orientation of the TLC plate such that the mobile phase develops in a direction that crosses the boundary between the first and second separating agent layers (also referred to as the "second direction"); immersing the edge of the plate in the mobile phase; and carrying out development with the mobile phase such that the aforementioned spots in the first separating agent layer traverse this boundary and migrate into the second separating agent layer.

The second direction can be in the range from greater than 0° with respect to the first direction up to and including 90° with respect to the first direction, and, viewed from the perspective of the accuracy of the maintenance of the positional relationship of the spots for the first mobile phase, is preferably from 45 to 90°, more preferably from 60 to 90°, and even more preferably is 90°.

The mobile phase in the first step may be the same as or different from the mobile phase in the third step. For example, when the mobile phase used in the third step is more polar than the mobile phase in the first step, spot migration from the first separating agent layer into the second separating agent layer can be carried out more rapidly.

Water, an aqueous salt solution, an organic solvent, or a mixed solvent of the preceding may be used for the mobile phase (eluent). A single organic solvent may be used or two or more organic solvents may be used. The aqueous salt solution can be exemplified by an aqueous copper sulfate solution and perchlorate. The organic solvent can be exemplified by alcohols such as methanol, ethanol, and isopropanol; ketones such as acetone and ethyl methyl ketone; ethers such as tetrahydrofuran and dioxane; nitriles such as acetonitrile; sulfoxides such as dimethyl sulfoxide; sulfones such as sulfolane; esters such as ethyl acetate; amides such as dimethylformamide; hydrocarbons such as pentane, hexane, and petroleum ether; aromatic hydrocarbons such as benzene, toluene, and xylene; and halogen compounds such as methylene chloride, chloroform, bromoform, chlorobenzene, and bromobenzene. Viewed from the perspective of stabilizing the component or components that are to be detected, a suitable amount of an acid or base may be added to the mobile phase. The acid can be exemplified by acetic acid, propionic acid, and tetrafluoroacetic acid, and the base can be exemplified by diethylamine, monoethanolamine, and triethylamine.

The step of detecting a spot that has migrated into the second separating agent layer by exposure to ultraviolet light or by a color-development treatment with a coloring agent (the fourth step) can be performed in the same manner as in ordinary methods for detecting a spot in TLC by exposure to ultraviolet radiation or a color-development treatment with a coloring agent, with the exception that spots in the second separating agent layer are the targets for detection.

The first separating agent layer is formed by a first separating agent, which has an optical response to ultraviolet light or a coloring agent. Here, the optical response to ultraviolet light denotes an ultraviolet light-induced emission, e.g., fluorescence, or the absorption of the ultraviolet light. The optical response to a coloring agent denotes color development induced by the coloring agent.

The first separating agent layer can be formed in the same manner as for the thin layer of an ordinary TLC plate, with the exception that the first separating agent layer is formed by the first separating agent.

The first separating agent comprises a separating agent component that has the aforementioned optical response. This first separating agent can be exemplified by a supported-type separating agent comprising a carrier and the aforementioned separating agent component supported on or bonded to the carrier and by a particle consisted of the aforementioned separating agent component. The first separating agent in the present invention is preferably a separating agent for optical isomers, with which the facile detection of a sample by TLC has generally been regarded as highly problematic due to the capabilities and properties of the separating agent.

The aforementioned carrier is preferably a porous material considered from the standpoint of raising the separation performance. This carrier can be exemplified by synthetic polymers such as crosslinked polystyrene, crosslinked acrylic polymers, and epoxy polymers; cellulose and crosslinked cellulose in which cellulose has been strengthened by crosslinking; polysaccharides such as crosslinked materials such as crosslinked agarose, crosslinked dextran, and crosslinked mannan; and inorganic substances such as alumina, silica gel, mesoporous silica gel, zeolite, diatomaceous earth, molten silica, clay minerals, zirconia, and metals.

A low molecular weight separating agent having the aforementioned optical response or a high molecular weight separating agent having the aforementioned optical response can be used for the separating agent component in the first separating agent. The low molecular weight separating agents can be exemplified by ligand exchange-type separating agents, charge transfer-type (π-π) separating agents, hydrogen bonding-type separating agents, inclusion-type separating agents, ionic bonding-type separating agents, intercalation-type separating agents, crown ethers and their derivatives, and cyclodextrins and their derivatives. The high molecular weight separating agents can be exemplified by polysaccharide derivatives, polyamides, polymethacrylate esters, polyacrylamides, proteins, and tartaric acid derivatives. The polysaccharide derivatives can be exemplified by the polysaccharide derivatives used for separating agents for optical isomers and comprising a polysaccharide and an aromatic ester group, aromatic carbamoyl group, aromatic ether group, or carbonyl group substituted for all or a portion of the hydroxyl groups or amino groups in the polysaccharide. Examples here are the phenylcarbamate derivatives of cellulose, the phenyl ester derivatives of cellulose, the phenylcarbamate derivatives of amylose, and the phenyl ester derivatives of amylose. The phenyl group in these derivatives may have one or more substituents selected from the group consisting of $C_{1-20}$ hydrocarbons and halogens.

The second separating agent layer is formed by a second separating agent having an optical response that is different from that of the first separating agent. This different optical response means that the one of the optical responses induced by exposure to ultraviolet light or a color-development treatment with a coloring agent differs from the other of the optical responses induced by exposure to ultraviolet light or a color-development treatment with a color agent, to a degree that enables optical discrimination between them based on color or brightness. The second separating agent may or may not have the capacity to separate a component in the sample. Viewed from the perspective of an accurate detection of the positional relationship of the spots in the first separating agent layer, the second separating agent preferably does not have the capacity to separate a component in the sample. This second separating agent can be exemplified by the separating agents and carriers already described above and is preferably a carrier.

The particle sizes of the first and second separating agents can be set in accordance with the objective for the detection method of the present invention. For example, when the objective is to investigate the conditions for medium-pressure column chromatography, the particle size is preferably at least 10 μm, more preferably from 10 to 100 μm, and even more preferably from 20 to 100 μm from the perspective of obtaining results that are applicable to medium-pressure chromatography. The particle sizes of the individual separating agents may be the same as each other or may differ from one other. The particle size of each separating agent may be the catalog value, or the average particle size measured using a common particle size analyzer may be used.

When component detection in the fourth step is performed using an optical response brought about by exposure to ultraviolet light, the second separating agent preferably also contains a fluorescent indicator from the standpoint of achieving a more accurate detection. The known fluorescent indicators can be used for this fluorescent indicator, for example, magnesium tungstate or a manganese-containing zinc silicate. The content of the fluorescent indicator can be set according to the range in which component separation is possible and will generally be from 0.1 to 5 mass parts per 100 mass parts of the second separating agent.

When component detection in the fourth step is performed using an optical response brought about by a coloring agent, a known technology can be used for the coloring agent and for the color-development treatment therewith. The coloring agent can be exemplified by anisaldehyde solutions, phosphomolybdic acid solutions, iodine, ninhydrin solutions, aqueous potassium permanganate solutions, DNPH solutions, manganese chloride solutions, and Bromocresol Green solutions. The color-development treatment can be exemplified by treatments in which color development is brought about by applying the coloring agent to the TLC plate by coating or broadcasting or exposing the TLC plate to the coloring agent and as necessary heating the TLC plate.

The optical response of the sample components is the same as the optical response of the first separating agent in the present invention. Here, the optical response being the same denotes that the one of the optical responses cannot be optically discriminated based on color or brightness from the other of the optical responses. The detection method according to the present invention makes possible a simple and convenient detection of the separation in TLC by the first separating agent of a component in the sample that is separated by at least the first separating agent and that cannot be optically detected on the first separating agent.

The TLC plate of the present invention as described herebelow is preferably used for the TLC plate for the detection method of the present invention.

The TLC plate of the present invention has a flat plate-shaped support, a first separating agent layer formed on the surface of this support, and a second separating agent layer adjacent thereto.

The flat plates generally used for TLC plates can be used for the support. This support can be exemplified by flat plates made of glass, resin, metal, or paper. There are no particular limitations on the shape of the support, but a rectangular or square shape is preferred from the standpoint of the compact execution in preferred directions of sample development in the first separating agent layer followed by spot development from the first separating agent layer into the second separating agent layer. The size of the flat plate is also not particularly limited, but viewed in terms of the convenience in handling, development time, and economics is preferably from 1 to 6,000 cm$^2$, more preferably from 2 to 410 cm$^2$, and even more preferably from 5 to 75 cm$^2$. There are no particular limitations on the thickness of the flat plate within the range that permits use in the detection method of the present invention.

Two or more separating agents having different optical responses and selected from particulate separating agents having a particle size of at least 10 μm as described above can be used for the first and second separating agents. The first separating agent layer can be formed by coating the support with a first slurry containing the first separating agent and a coating solvent and as necessary subjecting the layer thereby formed to further drying. The second separating agent layer can be formed by coating the support with a second slurry containing the second separating agent and a coating solvent and as necessary subjecting the layer thereby formed to further drying.

The first and second separating agent layers can be formed using the methods known for the fabrication of TLC plates. Thus, the first and second separating agent layers can be formed by coating the first and second slurries on the surface of the support using a spreader or by spraying the first and second slurries on the surface of the support. There are no particular limitations on the sequence for forming the first and second separating agent layers, and the one layer may be formed followed by the formation of the other layer or both layers may be formed at the same time.

Water, an organic solvent, or a mixed solvent of the preceding may be used for the coating solvent. The organic solvent can be exemplified by alcohols such as methanol, ethanol, and isopropanol; ketones such as acetone and ethyl methyl ketone; ethers such as tetrahydrofuran and dioxane; nitriles such as acetonitrile; sulfoxides such as dimethyl sulfoxide; sulfones such as sulfolane; esters such as ethyl acetate; amides such as dimethylformamide; hydrocarbons such as pentane, hexane, and petroleum ether; aromatic hydrocarbons such as benzene, toluene, and xylene; and halogen compounds such as methylene chloride, chloroform, bromoform, chlorobenzene, and bromobenzene.

The coating solvent is preferably a mixed solvent of a water-soluble organic solvent and water and more preferably is a mixed solvent of water and an alcohol and even more preferably is a mixed solvent of water and ethanol. The content of the alcohol in this mixed solvent is preferably from 0.1 to 50 mass %, more preferably from 10 to 40 mass %, and even more preferably from 20 to 30 mass %. Viewed from the perspective of preventing disarrangement of the boundary between the first and second separating agent layers and realizing an excellent spot migration from the first separating agent layer to the second separating agent layer, the first and second slurries preferably use the same type of coating solvent and more preferably use the same coating solvent composition.

The coating solvent content in the first and second slurries can be determined based on a consideration of the uniformity and layer thickness of the separating agent layer to be formed and the economics, and, expressed per 100 mass parts of the first or second separating agent, is preferably 10 to 5,000 mass parts, more preferably 50 to 1,000 mass parts, and even more preferably 100 to 300 mass parts for both the first and second slurries.

The first and second slurries preferably also contain a binder in order to improve the strength of the separating agent layer to be formed. A component that displays a binding performance that will form the separating agent layer on the support surface can be used as this binder. This binder can be exemplified by inorganic binders such as gypsum and colloidal silica; organic fibers such as microfibrillated cellulose; thickeners such as aqueous base-soluble copolymers, hydroxyethyl cellulose, and carboxymethyl cellulose; and organic binders such as polyvinyl alcohol and acrylic acid. A single binder or two or more binders may be used.

The binder content in the first and second slurries can be set based on a consideration of the strength of the separating agent layer to be formed and also based on a consideration of the rate of development of the mobile phase in the first or second separating agent layer. Larger amounts of binder are preferred in order to improve the strength of the separating agent layer to be formed, but the rate of development of the mobile phase in a separating agent layer generally slows in proportion to the increase in the amount of binder addition. When in the previously described first step the rate of development of the mobile phase in the second separating agent layer is substantially smaller than the rate of development of the mobile phase in the first separating agent layer, a phenomenon is then produced in which the sample spots develop while veering toward the second separating agent layer with reference to the first direction and an accurate analysis of sample separation by the first separating agent layer may then not be possible. When, in contrast, the rate of development of the mobile phase in the second separating agent layer is substantially larger than the rate of development of the mobile phase in the first separating agent layer, a phenomenon is then produced in which the sample spots develop while veering away from the second separating agent layer with reference to the first direction and an accurate analysis of sample separation by the first separating agent layer may then not be possible. Viewed from the perspective of accurately comprehending the state of separation by the first separating agent layer, the sample spots preferable develop in the first direction (for example, perpendicularly) to the greatest degree possible when the sample is developed in the first separating agent layer.

On the other hand, when in the third step the rate of development of the mobile phase in the second separating agent layer is substantially larger than the rate of development of the mobile phase in the first separating agent layer when the spots traverse the boundary between the first and second separating agent layers, spot tailing is produced and component detection in the second separating agent layer is then made quite problematic. Viewed from the perspective of inhibiting this phenomenon and having the positional relationships and shapes of the spots in the development direction in the first separating agent layer also be preserved in the second separating agent layer, preferably the rate of development of the mobile phase in the first separating agent layer is the same as the rate of development of the mobile phase in the second separating agent layer or the rate of development of the mobile phase in the second separating agent layer is made somewhat smaller than the rate of development of the mobile phase in the first separating agent layer.

Given the preceding perspectives, the TLC plate of the present invention provides a value, when spot development has been performed in the first direction in the first separating agent layer, of not more than ±0.5 for the ratio W2/W1 of the spot migration distance W2 in the second direction in the first separating agent layer to the spot migration distance W1 in the first direction in the first separating agent layer. W1 represents the distance from the position of sample spot application in the first separating agent layer to the leading edge of the spot. W2 represents the distance in the second direction from the aforementioned position of spot application to the leading edge of the spot. W2/W1 is preferably not more than ±0.3 from the perspective of accurately comprehending the state of separation in the first separating agent layer; more preferably is a positive value from the perspective of inhibiting tailing; and even more preferably is not more than 0.1. Letting the position of sample spot application be 0, a positive is used for W2 for the second separating agent layer side from the position of spot application and a negative is used for the side of the position of spot application opposite from the second separating agent layer.

Viewed from the perspective of improving the layer strength and controlling the rate of development of the mobile phase, an inorganic binder and an organic binder are preferably used in combination for the binder in both the first and second slurries. Gypsum is preferably used for the inorganic binder, while carboxymethyl cellulose is preferably used for the organic binder.

The binder contents in the first and second slurries can be established considering the strength of the layer to be formed and the generation of a suitable range for W2/W1. For example, the gypsum content in the first slurry, expressed per 100 mass parts of the first separating agent, is preferably 0.1 to 50 mass parts, more preferably 5 to 30 mass parts, and even more preferably 10 to 20 mass parts. The content of the organic binder in the first slurry, expressed per 100 mass parts of the first separating agent, is preferably 0.1 to 50 mass parts, more preferably 0.5 to 10 mass parts, and even more preferably 1 to 3 mass parts.

As an example, the gypsum content in the second slurry, expressed per 100 mass parts of the second separating agent, is preferably 0.1 to 50 mass parts, more preferably 1 to 30 mass parts, and even more preferably 2 to 8 mass parts. The content of the organic binder in the second slurry, expressed per 100 mass parts of the second separating agent, is preferably 0.1 to 50 mass parts, more preferably 0.5 to 10 mass parts, and even more preferably 2 to 4 mass parts.

The strength of the first and second separating agent layers should be a strength sufficient to withstand the storage and use associated with TLC, for example, a strength sufficient to prevent debonding and fracture of the separating agent layer during storage and use. W2/W1 can be determined in the first separating agent layer by, for example, spotting and developing a colored sample. Moreover, since the rate of development of the mobile phase slows as the separating agent layer becomes thicker and the rate of development of the mobile phase speeds up as the separating agent layer becomes thinner, W2/W1 can also be adjusted using the thickness of the first and second separating agent layers, as well as through the binder type and amount of binder incorporation.

The first and second slurries may additionally contain a dispersing agent from the perspective of bringing about a uniform dispersion of the binder on the surface of the dispersing agent. This dispersing agent can be exemplified by styrene/maleic anhydride polymers.

The thickness of the first and second separating agent layers can be set as appropriate in conformity to the intended use of the TLC plate. For example, viewed from the perspective of the application of the obtained results to medium-pressure column chromatography or use of the obtained results for compound fractionation or for reaction monitoring in the case of asymmetric synthesis reactions, the thickness of the separating agent layer is preferably 0.01 to 100 mm, more preferably 0.03 to 10 mm, and even more preferably 0.05 to 2 mm.

There are no particular limitations on the size of the TLC plate, and the size can be determined as appropriate in conformity to the separating agent, the sample, and the mobile phase. A large size is desirable based on a consideration of component separation, but the size is desirably not too large based on considerations of ease of handling and convenience of detection. The size of the first and second separating agent layers can be set as appropriate based on these considerations.

For example, the length (B) of the first separating agent layer in the first direction should be sufficiently large to bring about development of the sample in the first direction and can be established as appropriate considering the first separating agent, the sample, and the mobile phase. Considered from the perspective of providing a reliable processability and detection, the length B of the first separating agent layer in the first direction is preferably from 1 to 30 cm, more preferably from 3 to 20 cm, and even more preferably from 5 to 12 cm.

Considered from the perspective of providing a reliable processability and detection, the length (A1) of the second direction in the first separating agent layer is preferably 0.01 to 200 cm, more preferably 0.01 to 20 cm, and even more preferably 0.02 to 5 cm.

Considered from the perspective of providing a reliable processability and detection, the length (A2) of the second separating agent layer in the second direction is preferably 0.1 to 30 cm, more preferably 0.5 to 20 cm, and even more preferably 1 to 5 cm.

The ratio of A2 to A1 (A2/A1) is desirably larger based on a consideration of bringing about the migration by development with the mobile phase of the spots from the first separating agent layer into the second separating agent layer, but is desirably smaller based on considerations of the ease of handling and convenience of detection. Based on these considerations, the ratio A2/A1 is preferably from 0.1 to 20, more preferably from 0.1 to 10, and even more preferably from 0.1 to 5.

The ratio of B to A1 (B/A1) is desirably larger based on a consideration of the separation of the components in the sample in the first separating agent layer, but is desirably smaller based on a consideration of the processability. Based on these considerations, B/A1 is preferably 0.01 to 9,000, more preferably 0.2 to 4,000, and even more preferably 1 to 600.

The ratio of B to the sum of A1 and A2 (B/(A1+A2)) is desirably larger based on a consideration of the separation of the components in the sample in the first separating agent layer, but is desirably smaller based on a consideration of the processability and the migration of spots from the first separating agent layer into the second separating agent layer, particularly the migration of the spots of extract components. Based on these considerations, B/(A1+A2) is preferably 0.01 to 30, more preferably 0.1 to 30, and even more preferably 0.8 to 12.

There are no particular limitations on the shape of either the first separating agent layer or the second separating agent layer as long as these layers are adjacent to each other and satisfy the length conditions described above. The first and second separating agent layers preferably each have a rectangular shape from the standpoint of the processability, providing a clear and distinct display of the positional relationship of the spots in the first separating agent layer, and ease of forming the individual layers. More preferably, the first separating agent layer has a rectangular shape in which the long direction is the first direction and the second separating agent layer has a rectangular shape that has the same length as that of the first separating agent layer in the first direction and that has a size that satisfies the ratio A2/A1 described above.

The present invention will be further described with reference to the drawings. The present invention is described below using the example of a configuration for the separation and detection of optical isomers.

Figure 1:
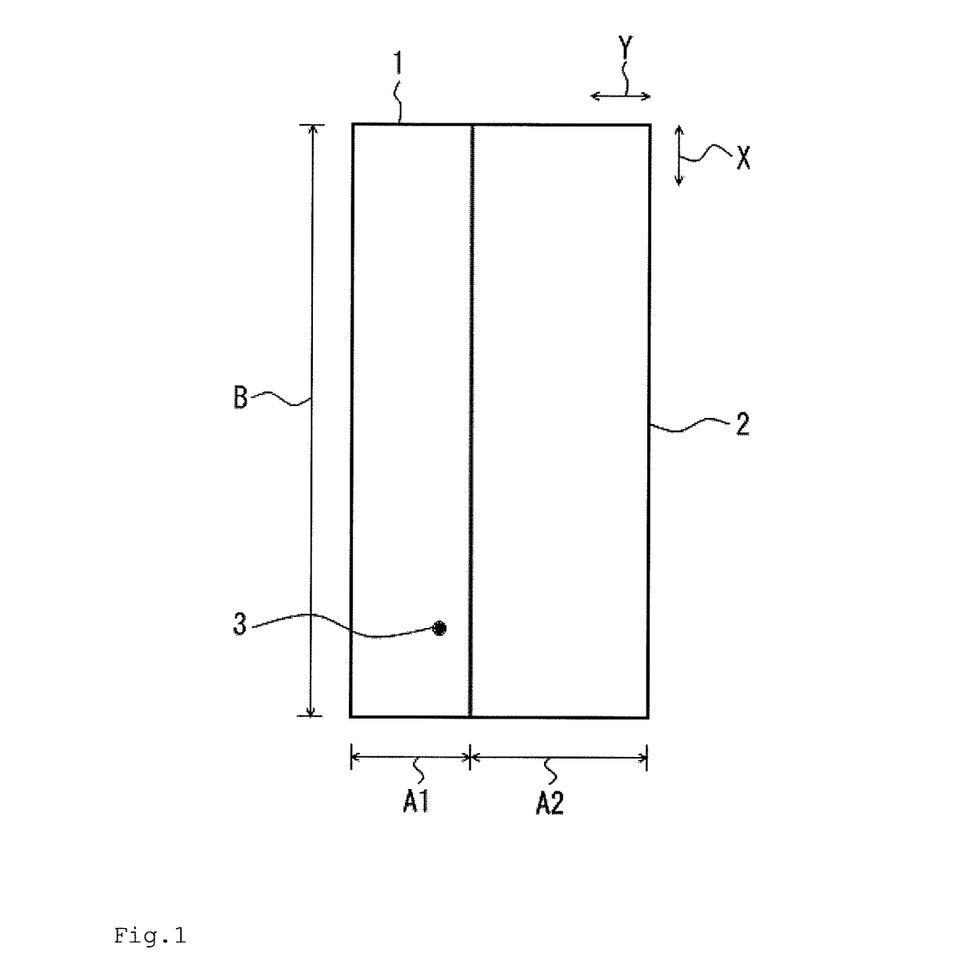
FIG. 1 is a diagram that shows the state when a spot of the sample solution has been applied to an example of a TLC plate of the present invention.

As shown in FIG. 1, the TLC plate of the present invention has a first separating agent layer 1 and a second separating agent layer 2, which are adjacently disposed on the surface of a quadrilateral support (not shown). For example, a glass plate is used for the support; a separating agent having the capacity to separate a component in the sample, for example, a separating agent for optical isomers in which a 3,5-dimethylphenylcarbamate derivative of amylose is chemically bonded to or supported on silica gel, is used for the first separating agent constituting the first separating agent layer 1; and a separating agent having an optical response different from that of the first separating agent, for example, silica gel, cellulose, or an octadecylsilylated silica gel provided by modifying the surface of a silica gel with the octadecyl group, is used for the second separating agent constituting the second separating agent layer 2.

The first separating agent layer 1 is formed by coating the surface of the support with a first slurry comprising the first separating agent, an aqueous ethanol solution, and gypsum and carboxymethyl cellulose. The second separating agent layer 2 is formed by coating the surface of the support, in a location adjacent to the first separating agent layer 1, with a second slurry comprising the second separating agent, an aqueous ethanol solution, gypsum and carboxymethyl cellulose, and a fluorescent indicator. The blending ratio for the binder in the first and second slurries (the blended amounts of the gypsum and carboxymethyl cellulose) is adjusted so as to provide—when development has been performed using Sudan and/or 1,4-aminoazobenzene as the standard sample—a value of not more than ±0.5 for the ratio (W2/W1) in the first separating agent layer 1 of the distance W2 in the second direction from the spot application location to the leading edge of a spot for the raffinate component, to the distance W1 in the first direction from the spot application location to the leading edge of the spot for the raffinate component. In addition to Sudan and 1,4-aminoazobenzene, a colored compound having a structure characteristic of or analogous to that of the sample that is the target of analysis by the TLC plate (for example, a structure with a skeleton that is the same or is analogous) can be selected as appropriate for the standard sample from among known substances.

The first and second separating agents each have a particle size of 20 µm, and the first and second separating agent layers each have a thickness of 150 µm. The first direction for this TLC plate is the direction that runs along the boundary between the first and second separating agent layers 1, 2 (the direction indicated by the arrow X in FIG. 1), and the second direction is the direction orthogonal to the X direction (the direction indicated by the arrow Y in FIG. 1).

The first separating agent layer 1 is formed in a rectangular shape wherein the X direction is the long direction. The second separating agent layer 2 is formed in a rectangular shape that shares a long edge with the first separating agent layer 1. The length B of the first and second separating agent layers 1, 2 in the X direction is 10 cm; the length A1 of the first separating agent layer 1 in the Y direction is 2 cm; and the length A2 of the second separating agent layer 2 in the Y direction is 2.5 cm.

First, letting the X direction be the vertical direction of this TLC plate, a spot of the sample solution is applied to the bottom of the first separating agent layer 1. The sample solution is, for example, a solution in a volatile solvent of the racemic body of optical isomers that have the ability to absorb ultraviolet light. The sample solution spot is applied, for example, using a capillary or a micropipette, to provide a spot with a diameter of not more than 2 mm at a position that is 1.5 cm from the lower edge of the TLC plate and 1.5 cm from the edge of the first separating agent layer 1 on the TLC plate on the side not adjacent to the second separating agent layer 2. The spot 3 of the sample solution is dried after its application.

Figure 2:
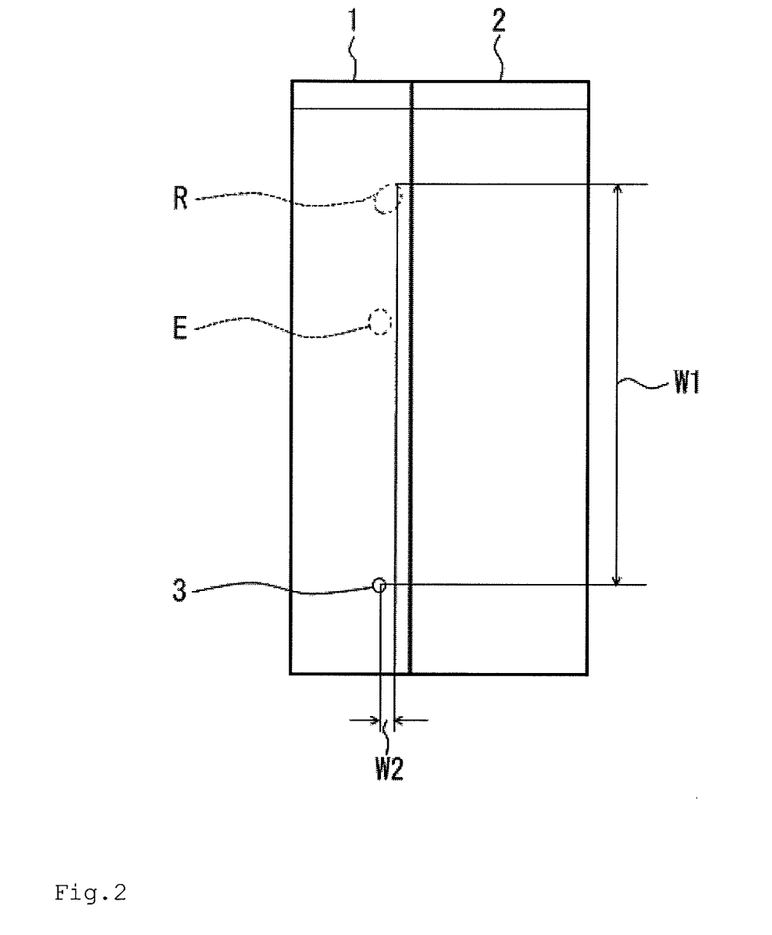
FIG. 2 is a diagram that shows the state when the sample has been developed in the first separating agent layer 1 of the TLC plate of FIG. 1.

The TLC plate spotted with the sample solution is loaded in a container (eluent tank) that can accommodate the TLC plate and that can also accommodate the mobile phase (eluent) at a depth of less than 1 cm. For example, an n-hexane/ethanol mixed solvent or an n-hexane/ethyl acetate mixed solvent may be used for the mobile phase. The mobile phase is drawn up in the X direction in the first and second separating agent layers 1, 2, and the raffinate component and extract component in the sample solution are developed in the first separating agent layer 1 accompanying the development of the mobile phase. As shown in FIG. 2, a spot R for the raffinate component and a spot E for the extract component are formed, although they cannot be identified by visual inspection.

When the mobile phase has reached the upper end of the TLC plate in the X direction as shown in FIG. 2, the TLC plate is removed from this sealed container and the mobile phase in the first and second separating agent layers 1, 2 is dried using a cold air current. As shown in FIG. 2, W1 is the migration distance of a spot in the first direction X in the first separating agent layer 1 and is represented by the distance between the leading edge of the spot in the first direction and the location of application of the sample solution spot. Also as shown in FIG. 2, W2 is the migration distance of the spot in the second direction Y in the first separating agent layer 1 and is represented by the distance in the second direction between the leading edge of this spot and the location of spot application.

Figure 3:
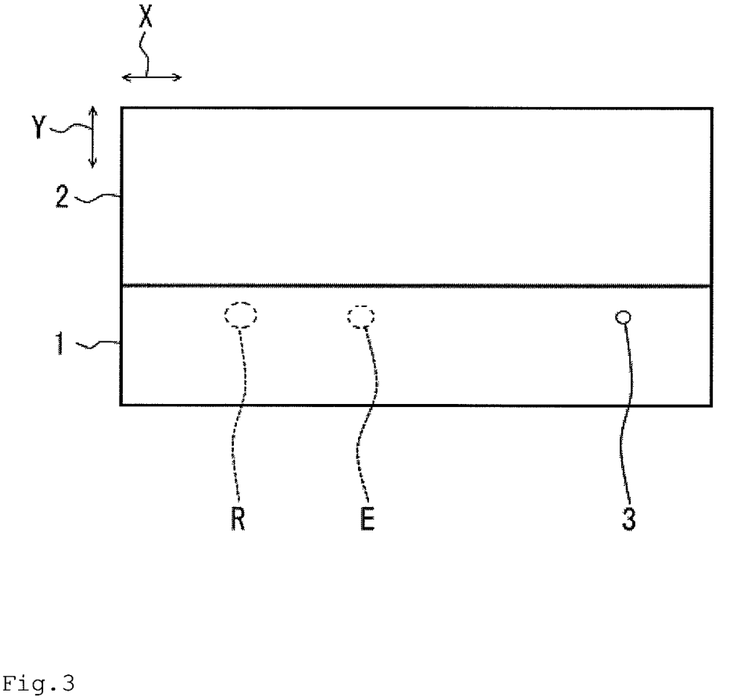
FIG. 3 is a diagram that shows the state when spots that have been developed in the first separating agent layer 1 are to be developed toward the second separating agent layer 2 on the TLC plate of FIG. 1.
Figure 4:
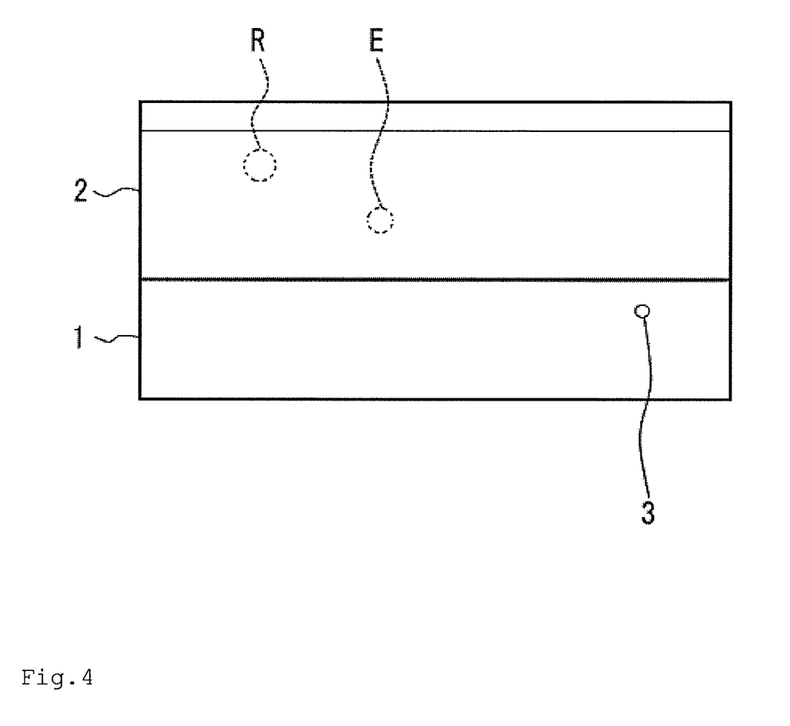
FIG. 4 is a diagram that shows the state when spots in the first separating agent layer 1 of the TLC plate of FIG. 1 have been developed toward the second separating agent layer 2.

Then, as shown in FIG. 3, the TLC plate is loaded in the aforementioned sealed container with the first separating agent layer 1 at the bottom and with the Y direction made the vertical direction of the TLC plate. The mobile phase at this time may be the same as or may differ from the mobile phase used in the previous sample development. The mobile phase is drawn up in the Y direction from the first separating agent layer 1 into the second separating agent layer 2, and, as shown in FIG. 4, the raffinate component and extract component in the first separating agent layer 1 migrate into the second separating agent layer 2 accompanying the development of the mobile phase. A spot R for the raffinate component and a spot E for the extract component are formed in the second separating agent layer 2, although they cannot be identified by visual inspection.

Figure 5:
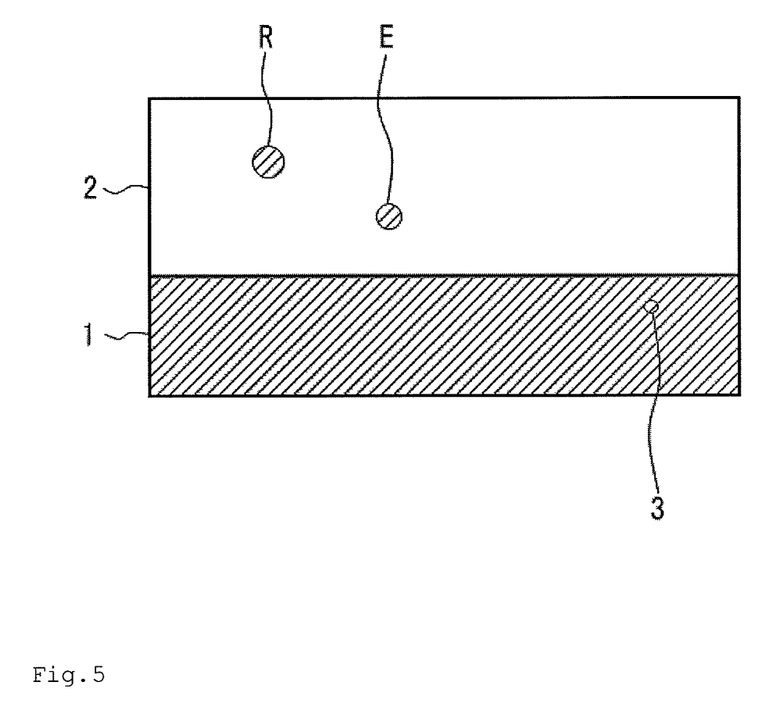
FIG. 5 is a diagram that shows the state of the TLC plate of FIG. 1 when the TLC plate having spots that have migrated into the second separating agent layer 2 is exposed to ultraviolet light.

When the mobile phase has reached the upper end of the TLC plate in the Y direction as shown in FIG. 4, the TLC plate is removed from this sealed container and the mobile phase in the first and second separating agent layers 1, 2 is dried using a cold air current in order to fix the spots R and E in the second separating agent layer 2. This TLC plate is exposed to ultraviolet light or a coloring agent is applied thereto and heating is carried out as necessary, thereby identifying the spots R and E and the first separating agent layer 1 based on the same optical response (for example, a dark region due to the absorption of ultraviolet light or a colored region due to color development with a coloring agent), as shown in FIG. 5.

In cases in which the state of separation of the components in the sample at the first separating agent layer is maintained or reflected in the second separating agent layer, the separation of a component in the sample by a first separating agent layer that does not permit the detection of the separation of the component in the sample by an optical response, can also be detected by bringing about the development of the spots of the first separating agent layer into the second separating agent layer in the third step without changing the orientation of the TLC plate (that is, bringing about the development into the second separating agent layer of the spots of the first separating agent layer in the third step while adopting the second direction from the range from greater than or equal to 0° to less than or equal to 90° with respect to the first direction). The second step can be omitted in such cases, and the present invention also encompasses these cases.

EXAMPLES

Example 1

TLC Plate Fabrication (Production of the First Separating Agent Layer)

6 g of the filler CHIRALPAK IA (Daicel Chemical Industries, Ltd., registered trademark of the same company) (also referred to as "filler IA"), 0.89 g gypsum, and 6 g of a 2% aqueous solution of CMC (carboxymethyl cellulose) 1110 (Daicel Chemical Industries, Ltd.) were added to a mixed solution of 3.03 g water and 3.01 g ethanol and this was thoroughly stirred while being exposed to ultrasound to obtain a slurry.

(Production of the Second Separating Agent Layer)

10.01 g silica gel (IR-60-5/20-U, for liquid chromatography, from Daiso Co., Ltd.), 0.50 g gypsum, 14.99 g of a 2% aqueous solution of CMC (carboxymethyl cellulose) 1110 (Daicel Chemical Industries, Ltd.), and 0.1 g manganese-containing zinc silicate were added to a mixed solution of 4.79 g water and 6.51 g ethanol and this was thoroughly stirred while being exposed to ultrasound to obtain a slurry.

(Coating)

These slurries were uniformly coated on the surface of a glass plate using a spreader for TLC plate fabrication that was equipped with a partition plate, to form separating agent layers in which A1 in FIG. 1 was 2 cm, A2 was 2.5 cm, and B was 10 cm, and the thickness of each layer was 150 µm. The average particle size of filler IA is 20 µm. The average particle size of the silica gel is 14.4 µm.

(Drying)

The slurry-coated TLC plate was dried in an air current and then vacuum dried for 3 hours at 60° C. under suction with a vacuum pump to obtain a TLC plate in which the filler IA layer was the first separating agent layer and the silica gel layer was the second separating agent layer.

Example 2

Example of the Optical Resolution of Trans-Stilbenzene Oxide

Approximately 1 µL of a 1% ethyl acetate solution of trans-stilbenzene oxide (t-SO) was spotted at a position that was approximately 1.5 cm from the bottom when the long direction of the TLC plate fabricated in Example 1 was placed vertically. The TLC plate was loaded with the sample spot down in an eluent tank that had been loaded with a mixed solvent that contained n-hexane and ethanol at 9:1 as the volume ratio and the sample was developed in the long direction of the IA separating agent layer.

After this first development, the TLC plate was dried on an interim basis with a cold air current and was rotated 90° to bring the IA separating agent layer to the bottom. The TLC plate was then loaded in the aforementioned eluent tank and the sample was further developed from the IA separating agent layer into the silica gel layer using ethanol.

After this second development, the TLC plate was dried with a cold air current and was exposed to ultraviolet light, thereby identifying the positions of the spots for the raffinate component and the extract component in the silica gel layer. The Rf values of the individual spots were calculated from the distance from the position of spot application to the position reached by the eluent in the first separating agent layer and the distance in the first developing direction in the second separating agent layer from the position of sample spot application to the center of the particular spot. When this was done, the Rf value for the raffinate component of the t-SO was 0.67 and the Rf value of the extract component was 0.58.

Example 3

Example of the Optical Resolution of Flavanone

Approximately 1 µL of a 1% ethyl acetate solution of flavanone (FLV) was spotted to a TLC plate that had been fabricated as in Example 1, and development was carried out using the same method as in Example 2.

After the second development, the TLC plate was dried with a cold air current and was exposed to ultraviolet light, thereby identifying the positions of the spots for the raffinate component and the extract component in the silica gel layer. The Rf values were calculated as in Example 2, yielding an Rf value for the FLV raffinate component of 0.40 and an Rf value for the extract component of 0.29.

Example 4

Example of the Optical Resolution of Benzoin Ethyl Ether

Approximately 1 µL of a 1% ethyl acetate solution of benzoin ethyl ether was spotted to a TLC plate that had been fabricated as in Example 1, and development was carried out using the same method as in Example 2 with the exception that a mixed solvent containing n-hexane and ethyl acetate at a volume ratio of 9:1 was used for the eluent in the first development and ethyl acetate was used for the eluent in the second development.

After the second development, the TLC plate was dried with a cold air current and was exposed to ultraviolet light, thereby identifying the position of the spots for the raffinate component and the extract component in the silica gel layer. The Rf values were calculated as in Example 2, yielding an Rf value for the raffinate component of the benzoin ethyl ether of 0.57 and an Rf value for the extract component of 0.30.

Example 5

Example of the Optical Resolution of Hexobarbital

Approximately 1 μL of a 1% ethyl acetate solution of hexobarbital was spotted to a TLC plate that had been fabricated as in Example 1, and development was carried out using the same method as in Example 2 with the exception that a mixed solvent containing n-hexane and isopropanol at a volume ratio of 9:1 was used for the eluent in the first development and isopropanol was used for the eluent in the second development.

After the second development, the TLC plate was dried with a cold air current and was exposed to ultraviolet light, thereby identifying the position of the spots for the raffinate component and the extract component in the silica gel layer. The Rf values were calculated as in Example 2, yielding an Rf value for the raffinate component of the hexobarbital of 0.33 and an Rf value for the extract component of 0.21.

Example 6

Example of the Optical Resolution of Tröger's Base

Approximately 1 μL of a 1% ethyl acetate solution of Tröger's base (TB) was spotted to a TLC plate that had been fabricated as in Example 1, and development was carried out using the same method as in Example 2.

After the second development, the TLC plate was dried with a cold air current and was exposed to ultraviolet light, thereby identifying the position of the spots for the raffinate component and the extract component in the silica gel layer. The Rf values were calculated as in Example 2, yielding an Rf value for the raffinate component of the TB of 0.56 and an Rf value for the extract component of 0.41.

Experimental Example

Investigation of the Amount of Binder Addition

Using gypsum and CMC 1110 at the mass parts given in the following Table 1 per 100 mass parts of the filler CHIRALPAK AD (from Daicel Chemical Industries, Ltd., registered trademark of the same company) (also referred to as "filler AD") and the previously described silica gel, TLC plates 1 to 6 were fabricated using different amounts of binder addition. Using the thusly fabricated TLC plates 1 to 6, approximately 1 μL of a 1% ethyl acetate solution of each sample, i.e., Sudan I and p-aminoazobenzene, was spotted at a position that was approximately 1.5 cm from the bottom when the long direction of the TLC plate was made vertical. The TLC plate was loaded with the sample spot down into an eluent tank that had been loaded with acetonitrile; the sample was developed in the long direction of the TLC plate; the distance W1 in the long direction of the TLC plate from the position of spot application to the leading edge of the spot and the distance W2 in the direction orthogonal to the aforementioned long direction and from the position of spot application to the leading edge of the spot were measured; and the ratio of W2 to W1 (W2/W1) was determined. For W2, the location of spot application was taken to be zero; the side toward the second separating agent layer was taken to be positive; and the opposite TLC plate edge side of the first separating agent layer was taken to be negative. Based on the fact that Sudan and p-aminoazobenzene have characteristic intrinsic colors, spot detection in the first separating agent layer was performed by visual inspection. The results are shown in Table 1. The results in Table 1 demonstrated that W2/W1 can be controlled by altering the amount of addition of the gypsum and CMC 1110.

TABLE 1

| | amount of binder addition (mass parts) | | | | W2/W1 (—) | |
|---|---|---|---|---|---|---|
| | first separating agent layer | | second separating agent layer | | | p-amino- |
| No. | gypsum | CMC1110 | gypsum | CMC1110 | Sudan I | azobenzene |
| 1 | 10 | 2.5 | 10 | 2.5 | 0.07 | 0.15 |
| 2 | 10 | 2.5 | 15 | 2.5 | 0.02 | −0.05 |
| 3 | 10 | 2.5 | 10 | 4.0 | 0.14 | 0.24 |
| 4 | 10 | 2.5 | 15 | 4.0 | 0.16 | 0.30 |
| 5 | 5 | 2.5 | 15 | 4.0 | 0.16 | 0.29 |
| 6 | 10 | 4.0 | 10 | 2.5 | −0.17 | −0.16 |

INDUSTRIAL APPLICABILITY

There has been demand in recent years for the further development of effective drug components and optical isomers useful as precursors therefor, and this has also been accompanied by demand for the development of technologies for identifying optical isomers and technologies that provide a more precise separation of optical isomers. The present invention makes possible the convenient identification by TLC of optical resolution by a separating agent that has a response to ultraviolet light, such as a polysaccharide derivative-based separating agent for optical isomers, and can more conveniently provide a material useful for setting the initial conditions in liquid chromatography and for optimizing the conditions in liquid chromatography. Accordingly, the present invention is expected to support the further expansion of technologies that involve chromatographic separation, such as the further development of useful optical isomers and the establishment of more productive methods of producing optical isomers.

EXPLANATION OF REFERENCE NUMERALS

1 first separating agent layer
2 second separating agent layer
3 sample solution spot
E spot of the extract component
R spot of the raffinate component
X arrow indicating the first direction in the present invention
Y arrow indicating the second direction in the present invention While the invention has been described in detail and with reference to specific embodiments thereof, it will be apparent to one skilled in the art that various changes and modifications can be made therein without departing from the spirit and scope thereof.

This application claims the benefit of Japanese Patent Application No. 2010-121140, filed on May 27, 2010, which is hereby incorporated by reference herein its entirety.

What is claimed is:

1. A sample detection method that uses a thin-layer chromatography plate having a first separating agent layer and a second separating agent layer adjacent thereto and that detects a component in a sample that exhibits an optical response to ultraviolet light or a coloring agent, the method comprising: a step of developing the sample in the first separating agent layer in a direction along the boundary between the first and second separating agent layers;
a step of drying a mobile phase in at least the second separating agent layer;
a step of changing the orientation of the thin-layer chromatography plate and developing a spot in the first separating agent layer into the second separating agent layer; and
a step of detecting a spot that has migrated into the second separating agent layer by exposure to ultraviolet light or by a color-development treatment with a coloring agent, wherein
the first separating agent layer is formed by a first separating agent, which has the optical response,
the second separating agent layer is formed by a second separating agent, which has an optical response that is different from that of the first separating agent, and
the optical response of the component is the same as the optical response of the first separating agent,
the first separating agent is a separating agent for optical isomers, and
the separating agent for optical isomers contains a polysaccharide derivative comprising a polysaccharide and an aromatic ester group, aromatic carbamoyl group, or aromatic ether group substituted for all or a portion of the hydroxyl groups or amino groups in the polysaccharide,
the first separating agent layer is formed by coating a support with a first slurry containing the first separating agent and a coating solvent,
the second separating agent layer is formed by coating the support with a second slurry containing the second separating agent and a coating solvent, and gypsum and an organic binder are used in combination as the binder in both the first and second slurries,
the gypsum content in the first slurry, expressed as per i00 mass parts of the first separating agent, is 5 to 30 mass parts and the content of the organic binder in the first slurry, expressed as per i00 mass parts of the first separating agent, is 0.5 to 10 mass parts, and
the gypsum content in the second slurry, expressed as per 100 mass parts of the second separating agent, is 1 to 30 mass parts and the content of the organic binder in the second slurry, expressed as per i00 mass parts of the second separating agent, is 0.5 to 10 mass parts.

2. A thin-layer chromatography plate that has a first separating agent layer, whose direction of development is a first direction, and, in a second direction that is orthogonal to the first direction, a second separating agent layer adjacent to the first separating agent layer, wherein the first separating agent layer is formed by a first separating agent, which has an optical response to ultraviolet light or a coloring agent; the second separating agent layer is formed by a second separating agent, which has an optical response that is different from that of the first separating agent; and when a spot has been developed in a first direction in the first separating agent layer, a ratio of the spot migration distance W2, in cm, in a second direction in the first separating agent layer to the spot migration distance WI, in cm, in the first direction in the first separating agent layer is not more than +/−0.5,
the first separating agent is a separating agent for optical isomers, and
the separating agent for optical isomers contains a polysaccharide and an aromatic ester group, aromatic carbamoyl group, or aromatic ether group substituted for all or a portion of the hydroxyl groups or amino groups in the polysaccharide,
the first separating agent layer is formed by coating a support with a first slurry containing the first separating agent and a coating solvent,
the second separating agent layer is formed by coating the support with a second slurry containing the second separating agent and a coating solvent, and gypsum and an organic binder are used in combination as the binder in both the first and second slurries,
the gypsum content in the first slurry, expressed as per 100 mass parts of the first separating agent, is 5 to 30 mass parts and the content of the organic binder in the first slurry, expressed as per i00 mass parts of the first separating agent, is 0.5 to 10 mass parts, and
the gypsum content in the second slurry, expressed as per 100 mass parts of the second separating agent, is 1 to 30 mass parts and the content of the organic binder in the second slurry, expressed as per 100 mass parts of the second separating agent, is 0.5 to 10 mass parts.

3. A method of producing a thin-layer chromatography plate that has a first separating agent layer and a second separating agent layer adjacent thereto,
the method comprising:
a step of forming a first separating agent layer by coating a support with a first slurry that contains a coating solvent and a first separating agent having an optical response to ultraviolet light or a coloring agent; and
a step of forming a second separating agent layer adjacent to the first separating agent layer, by coating the support with a second slurry that contains a coating solvent and a second separating agent having an optical response that is different from that of the first separating agent,
wherein
the same type of coating solvent is used for the first and second slurries,
the first separating agent is a separating agent for optical isomers, and
the separating agent for optical isomers contains a polysaccharide derivative comprising a polysaccharide and an aromatic ester group, aromatic carbamoyl group, or aromatic ether group substituted for all or a portion of the hydroxyl groups or amino groups in the polysaccharide,
gypsum and an organic binder are used in combination as the binder in both the first and second slurries,
the gypsum content in the first slurry, expressed as per 100 mass parts of the first separating agent, is 5 to 30 mass parts and the content of the organic binder in the first slurry, expressed as per 100 mass parts of the first separating agent, is 0.5 to 10 mass parts, and
the gypsum content in the second slurry, expressed as per 100 mass parts of the second separating agent, is 1 to 30 mass parts and the content of the organic binder in the second slurry, expressed as per 100 mass parts of the second separating agent, is 0.5 to 10 mass parts.

* * * * *

UNITED STATES PATENT AND TRADEMARK OFFICE
CERTIFICATE OF CORRECTION

PATENT NO.        : 9,234,881 B2                    Page 1 of 1
APPLICATION NO.   : 13/700223
DATED             : January 12, 2016
INVENTOR(S)       : Toshiharu Minoda et al.

It is certified that error appears in the above-identified patent and that said Letters Patent is hereby corrected as shown below:

In the claims,

Column 17, line 48 change "i00" to ---100---

Column 17, line 51 change "i00" to ---100---

Column 17, line 56 change "i00" to ---100---

Column 18, line 4 change "WI" to ---W1---

Column 18, line 24 change "i00" to ---100---

Signed and Sealed this
Second Day of August, 2016

Michelle K. Lee
*Director of the United States Patent and Trademark Office*